United States Patent [19]

Jacobson

[11] Patent Number: 4,710,462

[45] Date of Patent: Dec. 1, 1987

[54] CELL PROLIFERATION INHIBITOR AND METHOD OF PREPARATION

[75] Inventor: Bernard Jacobson, Lexington, Mass.

[73] Assignee: Boston Biomedical Research Institute, Boston, Mass.

[21] Appl. No.: 828,874

[22] Filed: Feb. 12, 1986

Related U.S. Application Data

[60] Continuation-in-part of Ser. No. 700,250, Feb. 11, 1985, abandoned, which is a division of Ser. No. 404,656, Aug. 3, 1982, Pat. No. 4,534,967, which is a continuation-in-part of Ser. No. 758,552, Jul. 24, 1985.

[51] Int. Cl.$^4$ ............................................ C12P 21/00
[52] U.S. Cl. ..................................... 435/68; 435/212; 435/219; 435/226; 530/350; 514/2
[58] Field of Search ................ 435/240, 241, 68, 212; 514/2; 530/350

[56] References Cited

PUBLICATIONS

Raymond et al.-ARVO Abst., (Apr. 1980), Abst. 8-10:15, pp. 145-146.
Jacobson et al., ARVO Abst., (Mar. 1981), Abst. 46, p. 216.

Primary Examiner—Sam Rosen
Attorney, Agent, or Firm—Weingarten, Schurgin, Gagnebin & Hayes

[57] ABSTRACT

This invention comprises preparing a cell proliferation inhibitor by a nonextractive method from a tissue which has neither a high content of collagen, nor proteoglycans. The source of inhibitor comprises hyalocyte cells, which release the inhibitor into culture medium. The inhibitor is isolated from the culture medium. By chromatographic separation fractions are provided of varying molecular weight. Fractions both below and above a molecular weight of about 13,000 daltons show inhibitory activity.

7 Claims, 2 Drawing Figures

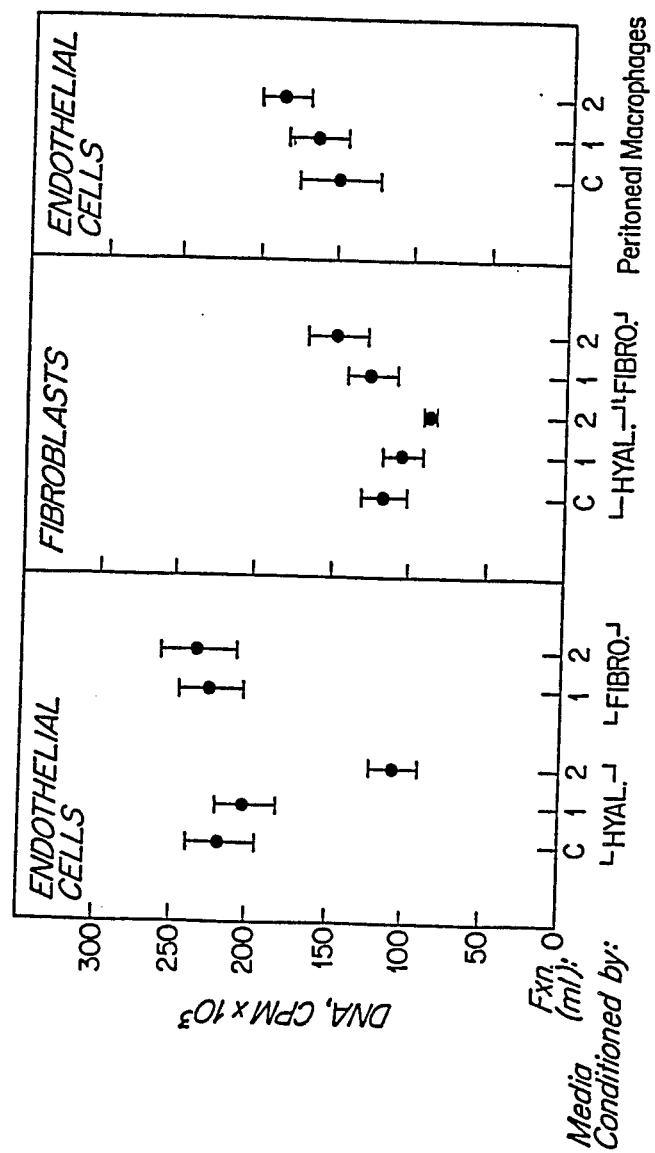

CELL PROLIFERATION INHIBITOR AND METHOD OF PREPARATION

The Government has rights in this invention pursuant to Grant No EY-00810 awarded by the Department of Health and Human Services.

BACKGROUND OF INVENTION

This is a continuation-in-part of Ser. No. 799,250 filed Feb. 11, 1985, now abandoned, which in turn is a division of Ser. No. 404,656 filed Aug. 3, 1982 now U.S. Pat. No. 4,534,967, and is also a continuation-in-part of Ser. No. 758,552 filed July 24, 1985 all of which applications are incorporated herein by reference.

This invention relates to a method of preparing an inhibitor of endothelial cell growth. The products of this method are useful in treating or preventing ocular neovascularization and reducing neovascularization in turmors.

Endothelial cells are a key component of blood vessels. Proliferation of vascular endothelial cells plays an important role in many bilogical processes. These include wound healing, formation of inflammatory granulation tissue, the organization of thrombi, the healing of large vessel defects and the repopoluation of endothelium in grafts. Normal adult vasular endothelium represents a slowly renewing population of cells. However, several pathological situations result in abnormal endothelial cell proliferation with the formation of unwanted new blood vessles This latter process is called "neovascularization."

Neovascularization of ocular tissues is one of the most important clinical problems in ophthalmology. In many disease states the various mature vascular beds of the eye grow beyond their normal limits. Diabetes mellitus is responsible for loss of vision in 12% of the total United States blind population and for 20% of the cases of new blindness in adults between the ages of 45 and 74. Retinopathy, the major cause of blindness in diabetes, is responsible in about 84% of blind diabetic patients. At some criticial point capillary endothelium begins to proliferate. The new retinal vessels may penetrate the internal limiting membrane of the retina and enter the vitreous where devastating hemorrhages may occur, leading to blindness. During the active, proliferative phase of diabetic retinopathy, neovascularization is also accompanied by fibrous tissue formation, which, when connected between the retinal and vitreous surfaces, can produce tractional elevation and tearing of the retina with subsequent retinal detachment. In the case of diabetic retinopathy, hemorrhage into the vitreous caused by traction on the new blood vessels is treated by removal of the vitreous. Retinal detachment is also sometimes treated by surgery.

The growth of solid tumors has long been recognized to be dependent on the ability of the tumor to induce the formation of new blood vessels by their hosts. The host blood vessels vascularize the solid tumor and provide it with nutrients which allow continued tumor growth.

One object of this invention is to provide an inhibitor of endothelial cell growth.

Another object of this invention is to provide such an inhibitor which will prevent neovascularization in ocular tissue and solid tumors.

Still another object of this invention is to reduce the need for surgery in diabetic retinopathy.

Further objects and advantages of this invention will be apparent from the description and claims which follow.

SUMMARY OF THE INVENTION

This invention broadly comprises preparing a cell proliferation inhibitor by a non-extractive method from a tissue which has neither a high content of collagen, nor proteoglycans. The source of inhibitor comprises hyalocyte cells, which upon being cultured release the inhibitor into the culture medium. The cells and culture medium are separated, and the inhibitor is isolated from the culture medium. By chromatographic separation, fractions of varying molecular weight are obtained. Fractions both below and above a molecular weight of about 13,000 daltons show inhibitory activity.

A preferred non-extractive method for preparing an ihibitor of cell growth comprises directly liquefying vitreous gel in the absence of extraction solvent by application of shear forces to the gel so as to directly convert the gel into a liquid, as, for example, forcing the gel through a syringe or using sonic vibrations, then separation hyalocytes from the liquid, culturing the hyalocytes in a medium, separating the medium from the hyalocytes, and isolating from the medium a product having inhibitory activity.

DESCRIPTION OF DRAWINGS

FIGS. 2A and 2B are plots of the effect of hyalocyte-incubated and fibroblast-incubated media on endothelial cells and fibroblasts.

FIG. 2C is a plot of the effect of peritoneal macrophage-incubated medium on endothelial cells.

SPECIFIC EXAMPLE OF INVENTION

Figure 1:
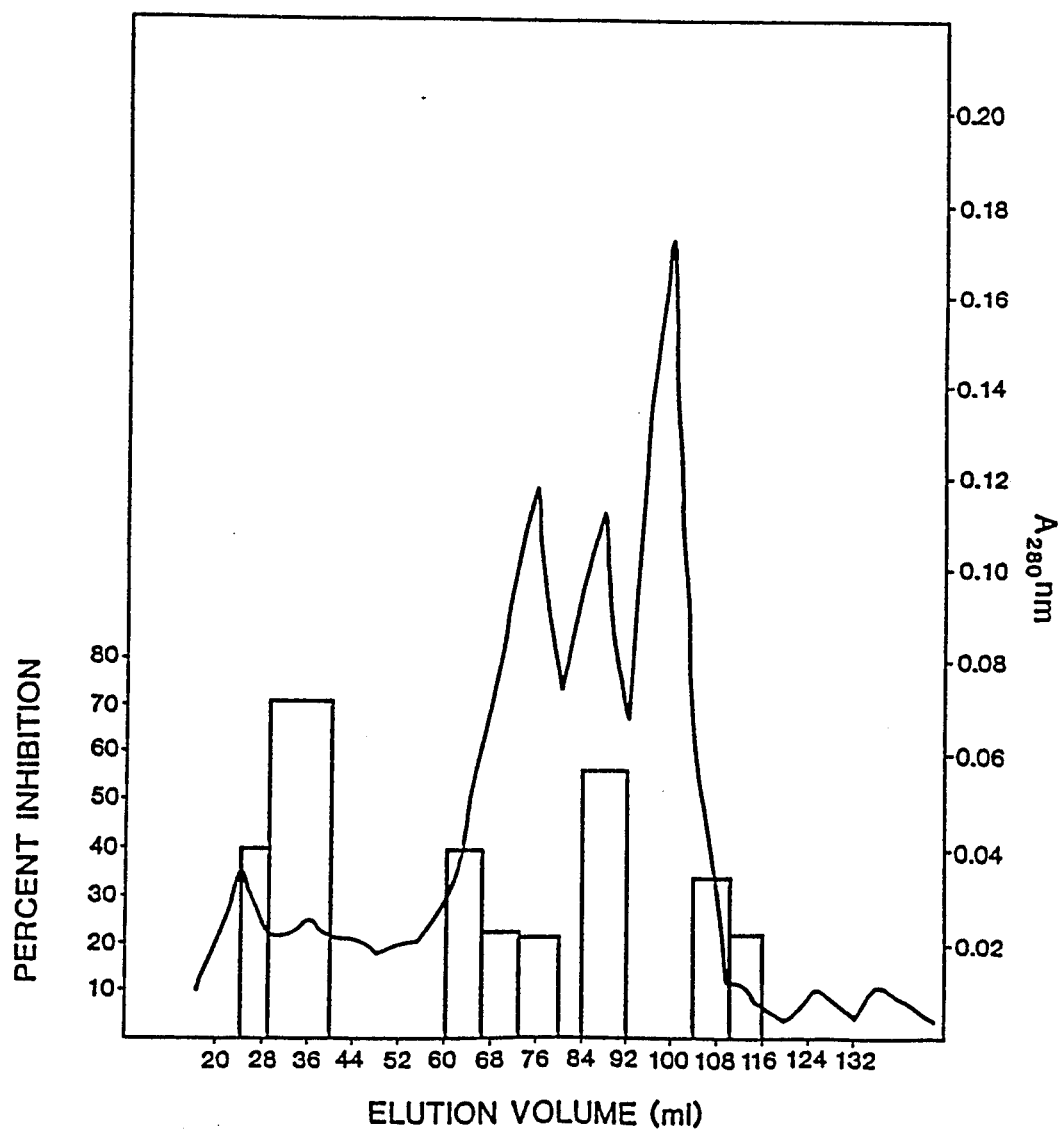
FIG. 1 is a plot of absorbance of collected fractions versus elution volume for culture medium conditioned by exposure to calf vitreous hyalocytes, chromatographed on a column of Bio-Gel P-10. It also shows the cell growth inhibitory activity of the various fractions.

The preparation of a hyalocyte culture and isolation of inhibitor fractions and their evaluation are described herein, having reference to the Procedures A, B and C described below. The following abbreviations are employed: DMEM means Dulbecco's Modified Eagles Medium; BME means Earle's Basal Medium; NBCS means newborn calf serum.

In the first step of the process for providing cell proliferation inhibitor from hyalocytes, the hyalocytes are isolated. In an exemplary procedure, calf eyes were trimmed of surrounding connective tissue, rinsed in running cold tap water and soaked for 30 minutes in a bactericidal/fungicidal solution (Duet, Madison Bionics). After rinsing the eyes again in distilled $H_2O$, the posterior gel containing the hyalocytes was isolated essentially as described in Balazs, Toth, Eckl and Mitchel (Exp. Eye Res. 3, 57–81, [1964]). The gel pieces were passed through a syringe (without a needle) to break the gel. The vitreous, containing the hyalocytes, was then incubated with sterile-filtered collagenase (1 mg/cc, Type III, Worthington Biochemical Corp.) in Earle's Basal Medium (abbreviated BME; contains Earle's salts, gultamine, glucose, vitamins and Gentamicin, without serum) at 37° C. until inspection showed the vitreous to be significantly reduced in viscosity. At this point, the cells were isolated by centrifugation at 1000 r/min in a Beckman TJ-6 centrifuge for 10 min.

Next, the isolated cells were suspended in fresh BME culture medium and kept for 18 hours in humidified 5% $CO_2$ in air without shaking, allowing the isolated cells to produce the desired cell-growth inhibitor. Each tube included cells from two eyes. After 18 hours, the cells were separated from the culture medium by centrifugation as described above.

The hyalocyte-conditioned culture medium containing the inhibitor was then either mixed with DMEM/10% newborn calf serum, sterile filtered and added to wells containing the cells on whose growth the conditioned medium is to be tested, in the range of concentrations and amounts/well described below in Procedure C, or subjected to liquid chromatographic fractionation as described in Procedure A to produce chromatographic fractions containing inhibitor of various molecular weights. Cell viability of the hyalocytes was well maintained up to at least 18 hours as demonstrated by the cells' 95% exclusion of trypan blue.

Fibroblasts for comparative testing purposes were obtained from either chick embryos of fetal bovine dermis by a standard method of dissociating the tissue with the enzyme trypsin, and grown in the same medium and atmosphere as described in Procedure B. After the cells were allowed to proliferate, they were trypsinized to release them from the original culture dishes, then transferred into 24-well plates for subsequent treatment with the cell proliferation inhibitor. When they reached 75% confluence, fresh medium was added and the cells were allowed to incubate for 18 hours. Medium was then collected from each well, contrifuged at 1000 r/min and the supernatants pooled. The pooled media were mixed, sterile filtered and added to the well containing cells to be tested, the range of concentrations and amount/well being as described in assay Procedure C.

Macrophages for comparative testing purposes were obtained from CD-1 strain white male mice (Charles River Breeding Laboratories). Five to eight cubic centrimeters of BME/20% NBCS was injected into the peritoneal cavity, circulated by gentle massage and then withdrawn. Three separate washers per mouse were pooled and spun at 1000 r/min for 5 minutes. Cells were resuspended in BME/20% NBCS and transferred to testing wells. Within 30 minutes, macrophages adhered to the flask surface and remaining unattached cells were removed by vigorously washing three times with the same medium. Subsequent treatment of the cells with 0.025% trypsin 24 hours later removed any remaining fibroblasts after which fresh medium (BME/20% serum) was added and the cells were incubated for 18 hours. The medium was then isolated and added to testing wells in the range of concentrations and amounts/well described in assay Procedure C.

The effect of hyalocyte-conditioned and fibroblast-conditioned medium on the growth of endothelial cells is shown in FIG. 2A, while the effect of medium conditioned by hyalocytes and fibroblasts on the growth of fibroblasts is shown in FIG. 2B. FIG. 2C illustrates the effect of peritoneal macrophage-conditioned medium on growth of endothelial cells. In FIG. 2A it is seen that medium conditioned by hyalocytes inhibits the growth of endothelial cells, whereas medium conditioned by fibroblasts does not. FIG. 2B demonstrates that medium conditioned by hyalocytes or by fibroblasts has little inhibitory effect on the growth of fibroblasts. FIG. 2C shows that medium conditioned by peritoneal macrophages has a slight stimulatory effect on growth of endothelial cells.

The medium conditoned by exposure to calf vitreous hyalocytes was chromatographed on a column of Bio-Gel P-10, with elution with 0.15M NaCl. FIG. 1 shows the chromatographic fractionation of hyalocyte-conditioned medium, absorbance of individual fractions being monitored at 280 nm for detection of protein-containing material, as shown by the jagged curve. The bars represent the percent inhibition of thymidine incorporation into endothelial cell DNA as discussed in Procedure C. FIG. 1 shows that the hyalocyte-conditioned medium posseses both high and low molecular weight materials having cell-growth inhibiting activity. Inhibitory activity appeared in the void volume material (molecular weight of more than approximately 13,000 daltons) represented by elution volumes 26–40 ml. Inhibitory material also appeared in three areas of the retarded volume, elution volumes 60–80 ml, 84–92 ml, and 106–116 ml, which contain materials of molecular weight lower than approximately 13,000 daltons.

PROCEDURES

A. Liquid Chromatographic Fractionation

Bio-Gel P-10 or porous glass beads are preferred. "Bio-Gel P-10" is a commerical polyacrylamide spherical beaded gel sized in particle sizes to permit fractionation in the range of 1,500 to 20,000 daltons. Other suitable media for chromatography include ion exchange cellulose or ion exchange gels. The liquid sample of material to be fractionated may be concentrated (optional) prior to column fractionation by placing it in cellulose tubing of 3,500 dalton cut-off point and covering the tubing with a dry material, such as polyethylene glycol, which draws the water out of the tubing.

The samples to be fractionated were loaded onto a chromatographic column containing the Bio-Gel P-10 and eluted with physiological saline, 0.15 M NaCl. The eluted fractions were monitored for the presence of protein by following ultraviolet absorption at 280 nm, as illustrated in FIG. 1.

Fractions eluted from the column were mixed with serum-containing tissue culture medium sterile filtered and added to endothelial cells according to Procedure C to test their effect on cell proliferation.

As an alternative to chromatography on Bio-Gel P-10, the medium containing the cell-growth inhibitor can be separated into high and low molecular weight fractions, containing respectively material of greater than 10,000 daltons and less than 10,000 daltons, by use of ultrafiltration employing a membrane filter whose molecular size cut-off point is approximately 10,000 daltons.

B. Endothelial Cenn Preparation

Vascular endothelial cells were prepared from calf aorta by the method of Macarak, et al. (Macarak, E. J. Howard, and B. V. Kefalides, N. Lab. Invest. 36, 62–67, [1977]) including treatment of the aortas with a tissue culture medium containing the enzyme collagenase. The endothelial cells were collected in a tissue culture medium, e.g., Dulbecco's Modified Eagles Medium (DMEM) containing 10% newborn calf serum (NBCS) plus penicillin, streptomycin and fungizone. The cells were then transferred to culture flasks or dishes and allowed to proliferate in culture medium. The cells were removed from the culture flask by the aid of trypsin, then transferred to 24-well plates for testing of the inhibitory factor. All cell cultures were kept in a humidified $CO_2$ incubator (5% $CO_2$ in air ) at 37° C.

C. Assay of Inhibition of Cell Proliferation

The assay procedure is based on cell proliferation being necessarily accompanied by the synthesis of new DNA. One of the constituents of DNA is the nucleoside thymidine. Addition or radioactive thymidine to the cell culture medium results in uptake of radioactive thymidine by the cells and its subsequent incorporation into newly synthesized DNA. A reduction of radioactive thymidine incorporation into newly synthesized DNA is indicative of a reduction in cell proliferation.

Material to be tested for cell growth inhibitory activity, such as aliquots of cell-conditioned medium or chromatographic fractions, were mized with culture medium in any of a range of concentrations from about 1% to about 40% (V/V), usually from 10–40% (V/V), then sterile filtered and added in amounts of about 0.5 cc per well to duplicate sets of wells already containing the cell type to be tested in 0.5 cc of culture medium. After 24 hours, 0.50 cc were removed from each well and a fresh aliquot of 0.50 cc of the fractions to be tested were added to the wells containing the cells. At the same time, 1 microcurie of radioactive thymidine (tritium-labelled) was also added to each well and the cells allowed to incubate for an additional 24 hours. the culture medium was then removed from the cell layer, the cells were briefly washed with fresh culture medium, and 0.5 M NaOH was added to each well and allowed to stand for 8 hours at 37° C. (this treatment extracts DNA from the cells). The contents of each well were transferred to separate test tubes and mixed with non-radioactive DNA (0.5 mg/tube). DNA (mixture of radioactive and non-radioactive) was then precipitated by addition of trichloroacetic acid (final concentration 30%) and collected on 0.45 $\mu$m pore size filters. The filters were dissolved in a solvent (e.g. Filtron X) and the radioactive DNA assayed in a liquid scintillation spectrometer. The amount of radioactive DNA in the cells treated with the various column fractions was compared to control cell cultures which received 0.15M NaCl.

Although the invention has been illustrated by use of particular examples, persons skilled in the art would appreciate that changes may be made without departing from the intended scope of the invention. Accordingly, the invention is not to be limited except by the scope of the appended claims.

What is claimed is:

1. A non-extractive method for preparing an inhibitor of cell growth, comprising directly liquefying vitreous gel in the absence of extraction solvent by application of shear forces to the gel so as to directly covert the gel into a liquid, incubating said liquid with collagenase to reduce its viscosity, separating hyalocytes from said collagenase-treated liquid, incubating said hyalocytes in a culture medium, separating said hyalocytes from the medium, chromatographically separating said medium into several fractions of varying molecular weight, and isolating from at least one of said fractions a product having cell growth inhibitory activity.

2. The method of claim 1 wherein the direct liquefaction is accomplished by forcing the gel through a small orifice.

3. The method of claim 1 wherein the direct liquefaction is accomplished by application of sonic vibrations.

4. The method of claim 1 wherein the product is isolated from a fraction having a molecular weight of less than approximately 13,000 daltons.

5. The method of claim 1 wherein the product is isolated from a fraction having a molecular weight in excess of approximately 13,000 daltons.

6. A high molecular weight inhibitor of cell growth made by the method of claim 5.

7. The method of claim 1 wherein said step of chromatographically separating is accomplished on Bio-Gel P-10.

* * * * *

UNITED STATES PATENT AND TRADEMARK OFFICE
CERTIFICATE OF CORRECTION

PATENT NO. : 4,710,462

DATED : December 1, 1987

INVENTOR(S) : Bernard Jacobson

It is certified that error appears in the above-identified patent and that said Letters Patent is hereby corrected as shown below:

Column 1, line 10, "Ser. No. 799,250" should read --Ser. No. 700,250--.

Column 1, line 20, "turmors." should read --tumors.--.

Column 1, line 23, "bilogical" should read --biological--.

Column 1, line 26, "repopoluation" should read --repopulation--.

Column 1, line 31, "vessles This" should read --vessels. This--

Column 1, line 43, "criticial" should read --critical--.

Column 2, line 18, "ihibitor" should read --inhibitor--.

Column 2, line 23, "separation" should read --separating--.

Column 3, line 21, "of fetal" should read --or fetal--.

Column 3, line 34, "the well" should read --the wells--.

Column 3, line 42, "washers" should read --washes--.

Column 4, line 3, "conditoned" should read --conditioned--.

Column 4, line 13, "posseses" should read --possesses--.

Column 4, line 44, "medium sterile" should read --medium, sterile--.

Column 4, line 55, "Cenn" should read --Cell--.

UNITED STATES PATENT AND TRADEMARK OFFICE
CERTIFICATE OF CORRECTION

PATENT NO. : 4,710,462
DATED : December 1, 1987
INVENTOR(S) : Bernard Jacobson

It is certified that error appears in the above-identified patent and that said Letters Patent is hereby corrected as shown below:

Column 5, line 9, "Addition or" should read --Addition of--.

Column 5, line 17, "mized" should read --mixed--.

Column 5, line 28, "hours. the" should read --hours. The--.

Column 6, line 15, "covert" should read --convert--.

Signed and Sealed this

Twenty-eighth Day of August, 1990

Attest:

HARRY F. MANBECK, JR.

*Attesting Officer*     *Commissioner of Patents and Trademarks*